United States Patent
Armoundas et al.

(10) Patent No.: US 7,336,995 B2
(45) Date of Patent: Feb. 26, 2008

(54) METHOD OF AND APPARATUS FOR TACHYCARDIA DETECTION AND TREATMENT

(75) Inventors: Antonis A. Armoundas, Cambridge, MA (US); Richard J. Cohen, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 333 days.

(21) Appl. No.: 10/299,415

(22) Filed: Nov. 19, 2002

(65) Prior Publication Data

US 2004/0098061 A1 May 20, 2004

(51) Int. Cl.
*A61N 1/362* (2006.01)
(52) U.S. Cl. .......................................... 607/9; 600/513
(58) Field of Classification Search .............. 607/4–28; 600/515–518
See application file for complete search history.

(56) References Cited

U.S. PATENT DOCUMENTS

| | | | |
|---|---|---|---|
| 5,749,900 A * | 5/1998 | Schroeppel et al. | 607/4 |
| 5,921,940 A * | 7/1999 | Verrier et al. | 600/518 |
| 6,253,107 B1 * | 6/2001 | Albrecht et al. | 607/9 |
| 6,438,409 B1 * | 8/2002 | Malik et al. | 600/512 |
| 2002/0138106 A1 * | 9/2002 | Christini et al. | 607/9 |

* cited by examiner

*Primary Examiner*—Scott M. Getzow
(74) *Attorney, Agent, or Firm*—Sam Pasternak; Choate Hall & Stewart LLP

(57) ABSTRACT

Method and apparatus for preventing heart rhythm disturbances by recording cardiac electrical activity, measuring beat-to-beat variability in the morphology of electrocardiographic waveforms, and using the measured beat-to-beat variability to control the delivery of drug therapy and electrical impulses to the heart.

39 Claims, 5 Drawing Sheets

METHOD OF AND APPARATUS FOR TACHYCARDIA DETECTION AND TREATMENT

FIELD OF THE INVENTION

The present invention relates to methods and apparatus for preventing an adverse clinical event. The adverse clinical event includes, but is not limited to, adverse cardiovascular events such as occurrences of serious heart rhythm disturbances such as ventricular fibrillation, tachyarrhythmia, bradyarrhythmia, myocardial infarction, sudden cardiac death, and related maladies such as loss of consciousness, development of diminished cerebral function. The risk of the adverse clinical event is determined through electrocardiogram analysis.

BACKGROUND OF THE INVENTION

Cardiovascular disease is the greatest cause of morbidity and mortality in the industrialized world. It not only strikes down a significant fraction of the population without warning but also causes prolonged suffering and disability in an even larger number. Sudden cardiac death (SCD) is prevalent in the population, however it is difficult to treat because it is difficult to predict in which individuals it will occur, and it often occurs without warning, in an out of a hospital setting. It is widely acknowledged that use of implantable cardioverter defibrillators has reduced the incidence of SCD in high risk patients.

With reference to FIGS. 1a and 1b, an implantable cardioverter defibrillator (ICD) 100 is an implantable device that detects the initiation of arrhythmias, such as ventricular tachycardia or fibrillation, and terminates them by delivery of one or more electrical impulses to the heart 102. Often the energy of these impulses is quite large compared to the energy of impulses delivered by an artificial pacemaker, which is used to pace the heart but not to terminate arrhythmias. The increased ease of ICD implantation as well as advances in ICD technology has led to a rapid growth in the rate of ICD implantation. However, ICDs generally are used to terminate an arrhythmia, such as ventricular tachycardia or fibrillation, only after the arrhythmia has started. This feature of ICD function may lead to patients losing consciousness once the arrhythmia starts and also leads to patients experiencing what may be very uncomfortable electrical discharges of the ICD. Frequent ICD discharge can lead to extreme psychological stress in many patients. Some patients have an ICD placed, only to suffer recurrent shocks and finally to have the device deactivated. (Stevenson W. G., et al., "Prevention of Sudden Death in Heart Failure", *J. Cardiovasc Electrophysiol* 2001; 12:112-4. The contents of this article and all articles cited below are hereby incorporated by reference into the present application as if reproduced in their entireties.) Recently, it was shown that a rapid and progressive electrophysiological deterioration during ventricular fibrillation that may explain the decreased probability of successful resuscitation after prolonged fibrillation. (Tovar O. H., et al., "Electrophysiological Deterioration During Long-Duration Ventricular Fibrillation", *Circulation* 2000;102:2886-91) Also, the more often the ICD discharges, the shorter is the life of its battery. Frequent ICD discharge can also damage the heart tissue itself and as a result may make the heart more susceptible to future arrhythmias. Thus it would be highly desirable to be able to be able to prevent arrhythmias from starting rather than terminating them after their initiation by administration of an electrical shock.

Arrhythmias such as ventricular tachycardia and fibrillation are often caused by an electrical mechanism called reentry. With reference to FIGS. 2A-2D, reentry involves a loop-like path of electrical activation 104 circulating through a region of heart tissue, re-entering regions 106 that had been previously activated in prior loops. In early ischemic arrhythmias, ventricular tachycardia and fibrillation have been shown to depend on reentrant excitation. Although reentrant excitation is thought to underlie a variety of benign and malignant cardiac rhythms, descriptions of the mechanisms that are involved in the development of reentry remain obscured. A major factor leading to the genesis of ventricular fibrillation during ischemia is dispersion of refractoriness. Dispersion of refractoriness is a measure of non-homogeneous recovery of excitability in a given mass of cardiac tissue (tissue is called refractory when it can not be re-stimulated until it has recovered). In normal myocardium the excitability is strictly proportional to the duration of repolarization. Reentry is the most likely mechanism of arrhythmia facilitated by enhanced dispersion of repolarization. The elements that are most often represented in the experimental or clinical models of arrhythmias attributed to reentry include non-uniform conduction, non-uniform excitability, and non-uniform refractoriness.

Ischemia alters refractoriness through its effects on resting potential and action potential duration. These effects are non-uniform during regional ischemia because of local variations in blood flow and diffusion of substrate and metabolites across the ischemic boundary. The resulting non-uniformity in refractoriness undoubtedly contributes to the increased vulnerability of an ischemic heart to fibrillation. An important mechanism for enhancing dispersion of refractory period is alternation of the action potential from beat to beat.

Action potential alternans involves an alternating sequence in which the shape of the action potential (the wave-like pattern of variation of a cell's transmembrane potential) associated with an individual cardiac cell changes on an every other beat basis (as shown in the monophasic action potentials of FIG. 3 between beat 108 and beat 110). If the duration of the action potential alternates on an every other beat basis, then the duration of refractory period also alternates in duration because the refractory period is generally roughly comparable to the duration of the action potential. Thus action potential alternans creates a situation in which a region of the myocardium has a long refractory period on an every other beat basis. On these alternate beats, a region with action potential alternans can create islands of refractory tissue that can cause fractionation of activation wavefronts. Thus, action potential alternans, which generally occurs in diseased tissue, can promote the development of reentry.

The presence of action potential alternans can be detected in an electrocardiogram as ST segment and/or T-wave alternans (repolarization alternans—see representative portions 112 and 114 of heart beats depicted in FIG. 4). In the surface electrocardiogram (ECG), repolarization alternans, has been correlated with the presence of ventricular vulnerability to arrhythmias in humans. In this application, we define repolarization alternans to be any change in the morphology of the ST segment or T-wave of the electrocardiogram occurring on an every other beat basis.

Computer simulations of cardiac conduction processes in the inventors' laboratory predicted the relationship between the presence of electrical alternans and enhanced susceptibility to the onset of reentrant rhythm disturbances. (Smith, J. M., Cohen, R. J., "Simple finite-element model accounts for wide range of cardiac dysrhythmias", *Proc Natl Acad Sci* 1984;81:233-7.)

Specifically, the simulated ECGs have shown electrical alternans in myocardial cells that have refractory periods that exceed a threshold cycle length and as a result there will be a corresponding subpopulation of cells that can be at most be activated every second beat. This is reflected in electrical alternans in the ECG illustrated in FIG. 4. This process leads to wave-front fractionation thus being the predisposing factor to reentrant ventricular dysrhythmias.

Electrical alternans have been shown to precede ventricular fibrillation in dogs. (Smith, J M, et al., "Electrical alternans and cardiac electrical instability", *Circulation* 1988, 77:110-21; Nearing, B D, et al., "Dynamic tracking of cardiac vulnerability by complex demodulation of the T wave", *Science* 1991, 252:437-40.) A computer algorithm developed by the inventors that is sensitive to microvolt level oscillations of the surface ECG, in a series of animal experiments, revealed that coronary artery occlusion was also uniformly accompanied by a decrease in electrical stability (as measured by the ventricular fibrillation threshold) and occlusion was frequently accompanied by an increase in the observed alternation in ECG vector morphology. A description of the algorithm, which may be employed in the present invention for estimating repolarization alternans, and the noted results may be found in the following references: Smith, J. M., and Cohen, R. J., "Simple finite-element model accounts for wide range of cardiac dysrhythmias", *Proc Natl Acad Sci USA* 1984, 81:233-7; Adam, D. R., et al., "Fluctuations in T-wave morphology and susceptibility to ventricular fibrillation", *J. Electrocardiol* 1984, 17:209-18; and Clancy, E. A., et al., "A simple electrical-mechanical model of the heart applied to the study of electrical-mechanical alternans", *IEEE Trans Biomed Eng* 1991, 38:551-60.

In humans, alternation in electrical repolarization processes in the heart has been associated with increased vulnerability to ventricular arrhythmias under diverse pathophysiologic conditions such as myocardial ischemia (See Dilly, S. G., et al., "Electrophysiological alternans and restitution during acute regional ischaemia in myocardium of anaesthetized pig", *J Physiol* (London) 1988, 402:315-33; Dilly, S. G., et al., "Changes in monophasic action potential duration during the first hour of regional myocardial ischaemia in the anaesthetised pig", *Cardiovasc Res* 1987, 21:908-15; Lewis, T., "Notes upon alternation of the heart", *Q J Med* 1910, 4:141-144; Salerno, J. A., et al., "Ventricular arrhythmias during acute myocardial ischaemia in man. The role and significance of R-ST-T alternans and the prevention of ischaemic sudden death by medical treatment", *Eur Heart J* 1986, 7 Suppl A:63-75.), Prinzmetal's angina (See Kleinfeld, M. J., et al., "Alternans of the ST segment in Prinzmetal's angina", *Circulation*, 1977, 55:574-7; Reddy, C. V., et al., "Repolarization alternans associated with alcoholism and hypomagnesemia", *Am. J. Cardiol.*, 1984, 53:390-1), altered autonomic state (See Nearing, B. D., et al., "Potent antifibrillatory effect of combined blockade of calcium channels and 5-HT2 receptors with nexopamil during myocardial ischemia and reperfusion in dogs: comparison to diltiazem", *J. Cardiovasc. Pharmacol.*, 1996, 27:777-87; Cheng, T. C., "Electrical alternans. An association with coronary artery spasm", *Arch. Intern. Med.*, 1983, 143:1052-3; Kaufman, E. S., et al., "Influence of heart rate and sympathetic stimulation on arrhythmogenic T wave alternans", *Am. J. Physiol.*

*Heart Circ. Physiol.* 2000;279:H1248-55), electrolyte abnormalities (See Reddy; Kaufman; Shimoni, Z, et al., "Electrical alternans of giant U waves with multiple electrolyte deficits", *Am. J. Cardiol.* 1984, 54:920-1), and the long QT syndrome (See Schwartz, P. J., et al., "Electrical alternation of the T-wave: clinical and experimental evidence of its relationship with the sympathetic nervous system and with the long Q-T syndrome", *Am. Heart. J.*, 1975, 89:45-50; Platt, S. B., et al., "Occult T wave alternans in long QT syndrome", *J. Cardiovasc. Electrophysiol.*, 1996, 7:144-8; Armoundas, A. A., et al., "Images in cardiovascular medicine. T-wave alternans preceding torsade de pointes ventricular tachycardia", *Circulation*, 2000, 101:2550). Repolarization alternans in the form of macroscopically visible TWA has been associated anecdotally with a variety of conditions associated with an increased risk of ventricular arrhythmias (See H. H., et al., "Electrical alternans", *NY State J Med* 1948, 1:1164-1166; Kleinfeld, M, et al., "Pacemaker alternans: a review", *Pacing Clin. Electrophysiol.*, 1987, 10:924-33; Calabrese, G, et al., "ST-T segment alternans in ventricular tachycardia associated with inversion of the U wave in Prinzmetal angina during exercise test. Description of a clinical case", *G. Ital. Cardiol.*, 1990, 20:239-41; Cinca, J, et al., "The dependence of T wave alternans on diastolic resting period duration", *Eur. J. Cardiol.*, 1978, 7:299-309; Costello, D L, et al., "Echocardiographic examination in left ventricular alternans", *Chest*, 1979, 75:72-5; Fisch, C, et al., "T wave alternans: an association with abrupt rate change", *Am. Heart J.*, 1971, 81:817-21; Hashimoto, H, et al., "Potentiating effects of a ventricular premature beat on the alternation of the ST-T complex of epicardial electrograms and the incidence of ventricular arrhythmias during acute coronary occlusion in dogs", *J. Electrocardiol.*, 1984, 17:289-301; Hashimoto, H, et al., "Effects of calcium antagonists on the alternation of the ST-T complex and associated conduction abnormalities during coronary occlusion in dogs", *Br. J. Pharmacol*, 1981, 74:371-80; Konta, T, et al., "Significance of discordant ST alternans in ventricular fibrillation", *Circulation*, 1990, 82:2185-9; Puletti, M, et al., "Alternans of the ST segment and T wave in acute myocardial infarction", *J. Electrocardiol.*, 1980, 13:297-300.

Microvolt level T-wave alternans was first reported in 1982. (See Adam, D. R., et al., "Ventricular fibrillation and fluctuations in the magnitude of the repolarization vector", *IEEE Computers Cardiol.*, 1982, 241-244.) Subsequently, a series of studies led to the development of a spectral method to detect subtle microvolt level repolarization alternans, and developed a relationship between alternans and ventricular fibrillation thresholds in animal studies and susceptibility to ventricular arrhythmias in humans undergoing EPS testing. (See Smith; Adam; Ritzenberg, A. L., et al., "Period multupling-evidence for nonlinear behaviour of the canine heart", *Nature*, 1984, 307:159-61.) These studies experimentally linked repolarization alternans to increased susceptibility to ventricular tachyarrhythmias.

Recent studies have demonstrated that the presence of microvolt level repolarization alternans (generally not visible upon visual inspection of the electrocardiogram, but detectable using advanced signal processing techniques such as described in: Smith; Clancy; Platt; Rosenbaum, D. S., et al., "Electrical alternans and vulnerability to ventricular arrhythmias", *N. Engl. J. Med.*, 1994, 330:235-41; and Rosenbaum, D. S., et al., "Predicting sudden cardiac death from T wave alternans of the surface electrocardiogram: promise and pitfalls", *J. Cardiovasc. Electrophysiol.*, 1996, 7:1095-111), is associated with an increased risk of ventricular arrhythmias and sudden cardiac death. (See Verrier, R. L., et al., "Electrophysiologic basis for T wave alternans as an index of vulnerability to ventricular fibrillation", *J. Cardiovasc. Electrophysiol.*, 1994, 5:445-61; Verrier, R. L., et al., "Life-threatening cardiovascular consequences of anger in patients with coronary heart disease", *Cardiol. Clin.*, 1996, 14:289-307; Nearing, B. D., et al., "Personal computer system for tracking cardiac vulnerability by complex demodulation of the T wave", *J. Appl. Physiol.*, 1993, 74:2606-12; and Nearing, B. D., et al., "Quantification of ischaemia induced vulnerability by precordial T wave alternans analysis in dog and human", *Cardiovasc. Res.*, 1994, 28:1440-9).

In ECG tracings obtained from Holter monitoring, there has been evidence that repolarization alternans persist for long periods before the onset of an unstable heart rhythm like ventricular tachycardia or ventricular fibrillation (See Armoundas, A. et al., "Images in cardiovascular medicine. T-wave alternans preceding torsade de pointes ventricular tachycardia", *Circulation* 2000;101:2550.)

Thus, in both computer simulations and experimental reports electrical alternans has been shown to increase its magnitude in the stage preceding a malignant heart rhythm like ventricular fibrillation.

From the time heart rate variability (HRV) was first appreciated as a harbinger of sudden cardiac death in post myocardial infarction patients by Wolf et al. (Wolf, M. M., et al., "Sinus arrhythmia in acute myocardial infarction", *Med. J. Aust.* 1978, 2:52-3), numerous studies have established a significant relationship between HRV and susceptibility to lethal ventricular arrhythmias. (See Kleiger, R. E., et al., "Decreased heart rate variability and its association with increased mortality after acute myocardial infarction", *Am. J. Cardiol.*, 1987, 59:256-62; Malik, M, et al., "Heart rate variability in relation to prognosis after myocardial infarction: selection of optimal processing techniques", *Eur. Heart J.*, 1989, 10:1060-74; Bigger, J. T., et al., "Frequency domain measures of heart period variability and mortality after myocardial infarction", *Circulation*, 1992, 85:164-71; and Fallen, E. L., et al., "Spectral analysis of heart rate variability following human heart transplantation: evidence for functional reinnervation", *J. Auton. Nerv. Syst.*, 1988, 23:199-206.) A major issue has been how to describe HRV mathematically. The phenomenon of fluctuations in the interval between consecutive heart beats has been the subject of investigations using a wide range of methodologies including time domain (See Adamson, P. B., et al., "Unexpected interaction between beta-adrenergic blockade and heart rate variability before and after myocardial infarction. A longitudinal study in dogs at high and low risk for sudden death", *Circulation*, 1994, 90:976-82; and "Electrophysiology TfotEsocatNASoPa. Heart rate variability, standards of measurement, physiological interpretation and clinical use", *Circulation*, 1996, 93:1043-1065), frequency domain (See Bigger, J. T., et al., "Predicting mortality after myocardial infarction from the response of RR variability to antiarrhythmic drug therapy", *J. Am. Coll. Cardiol.*, 1994, 23:733-40; and Huikuri, H. V., et al., "Power-law relationship of heart rate variability as a predictor of mortality in the elderly", *Circulation*, 1998, 97:2031-6), geometric (Malik, M, et al., "Influence of the recognition artefact in automatic analysis of long-term electrocardiograms on time-domain measurement of heart rate variability", *Med. Biol. Eng. Comput.*, 1993, 31:539-44), and non-linear (See Schmidt, G, et al., "Nonlinear methods for heart rate variability", In: Malik M, Camm A J, eds. *Heart Rate Variability*. Armonk, N.Y.: Futura, 1995:87-98; Kanters, J. K., et al., "Short- and long-term variations in non-linear dynamics of heart rate variability", *Cardiovasc. Res.*, 1996, 31:400-9; and Kanters, J. K., et al., "Lack of evidence for low-dimensional chaos in heart rate variability. J Cardiovasc Electrophysiol 1994;5: 591-601), methods. With the general recognition of nonlinear dynamics theory in the mid 80's, it was proposed that HRV should be viewed as the result of nonlinear determinism in the regulatory systems governing the heart rate. Parameters indicative of possible low-dimensional nonlinear determinism include Lyapunov exponents, strange attractors and correlation dimensions (Grassberger, P, et al., "Measuring the strangeness of strange attractors", *Physica D.*, 1983, 9:183-208). For example, it has been suggested that the correlation dimension (CD) could be used to distinguish patients who develop ventricular fibrillation during the monitoring period from those who do not. (See Chon, K. H., et al., "Modeling nonlinear determinism in short time series from noise driven discrete and continuous systems", *Int. J. Bifurcation & Chaos*, 2000, 10:2745-2766.)

While ICDs currently are an effective therapy for the termination of heart rhythm disturbances (See Prystowsky, E. N., "Screening and therapy for patients with nonsustained ventricular tachycardia", *Am. J Cardiol.*, 2000, 86:K34-K39; Buxton, A. E., et al., "Nonsustained ventricular tachycardia", *Cardiol. Clin.*, 2000, 18:327-36, viii; and Buxton, A. E., et al., "Electrophysiologic testing to identify patients with coronary artery disease who are at risk for sudden death—Multicenter Unsustained Tachycardia Trial Investigators", *N. Engl. J. Med.*, 2000, 342:1937-45), their role is to deliver electrical impulses to terminate the arrhythmia rather than to prevent its onset. Thus, patients are being subjected to a serious arrhythmia for a period of time until therapy is delivered. Also, delivery of electrical impulses from the ICD may be painful and may damage the heart.

There remains, therefore, a need to prevent arrhythmias from initiating rather than treating them with what may be much higher energy electrical pulses after the arrhythmias have been initiated.

SUMMARY OF THE INVENTION

The present invention includes a method of preventing heart rhythm disturbances comprising: (i) detecting (and optionally recording) cardiac electrical activity (ii) measuring beat-to-beat variability in the cardiac electrical activity and (iii) using the beat-to-beat variability to control therapy to reduce the likelihood of heart rhythm disturbances. In certain embodiments, the beat-to-beat variability comprises repolarization alternans and/or heart rate variability.

The therapy comprises the delivery of one or more chemical substances and/or the delivery of electrical impulses to the heart. The electrical impulses may be controlled to alter the variability in the inter-beat interval or the diastolic interval.

A number of heart rhythm disturbances, including but not limited to tachyarrhythmias and bradyarrhythmias, are preventable by use of the invention.

In certain preferred embodiments, the electrical activity of the heart is recorded from a passive electrode within the heart.

In another embodiment, the measuring step is performed in an implanted device. In yet another embodiment, the therapy is delivered by an implanted device.

The implanted device optionally serves as a cardiac pacemaker or a cardiac cardioverter/defibrillator.

In another embodiment such device can contain a reservoir of chemical substance and delivery means, and deliver the compound to the patient at the appropriate times and dosages. This chemical substance may be a pharmacological agent that reduces the likelihood of a heart rhythm disturbance from occurring. The substance may be delivered into the blood stream or directly into the heart.

In another embodiment, the implantable device has means for generating electrical stimulating pulses of specified increasing energies and applying the pulses to body tissue at specified adjusted times appropriate for preventing the heart rhythm disturbance.

In a further embodiment, the measuring step further comprises identifying periods when there is an increased probability that a heart rhythm disturbance may occur. Periods of increased susceptibility to life threatening arrhythmias are characterized by increased levels of repolarization alternans or reduced heart rate variability. In these identified periods, therapy may be delivered.

The present invention will reduce the morbidity and mortality resulting from heart rhythm disturbances and the pain and complications associated with the termination of heart rhythm disturbances, in certain embodiments, by administering low energy electrical shocks. The present invention will also reduce the morbidity and mortality resulting from heart rhythm disturbances, by administering high energy electrical shocks such as occurs when an implanted cardioverter defibrillator (ICD) discharges to terminate ventricular tachycardia or fibrillation.

Application of early therapy by means of this invention utilizing an ICD will provide a significant improvement in preventing SCD. Currently, state of the art ICDs identify an abnormal heart rhythm based on the detection of its rate and morphology. However, failure or delay in detecting ventricular tachycardia or ventricular fibrillation are common. False detection of ventricular tachycardia or ventricular fibrillation is also a concern. In addition, the implications of an intervention after the development of an abnormal rhythm are not exactly known. Energy delivery in the myocardium, even if it succeeds to revert the heart rhythm to normal, is not an unharmful intervention either in short or long term of the cardiac function. Usually, an increase in energy delivered is required in repetitive shocks and as a result a possible accumulative damage in the cardiac tissue occurs. Moreover, depending on the type of the abnormal heart rhythm, an ICD may not succeed to lead the heart back to a normal rhythm.

The above methodology may not to be applied only in an ICD but also in a cardiac pacemaker. As used herein, the term implantable device (ID) refers to either an ICD or a cardiac pacemaker.

BRIEF DESCRIPTION OF THE DRAWING

Embodiments of the present invention are explained in greater detail below on the basis of FIGS. 1a through 5 of the attached drawing, where.

DETAILED DESCRIPTION OF CERTAIN PREFERRED EMBODIMENTS OF THE INVENTION

Figure 1A:
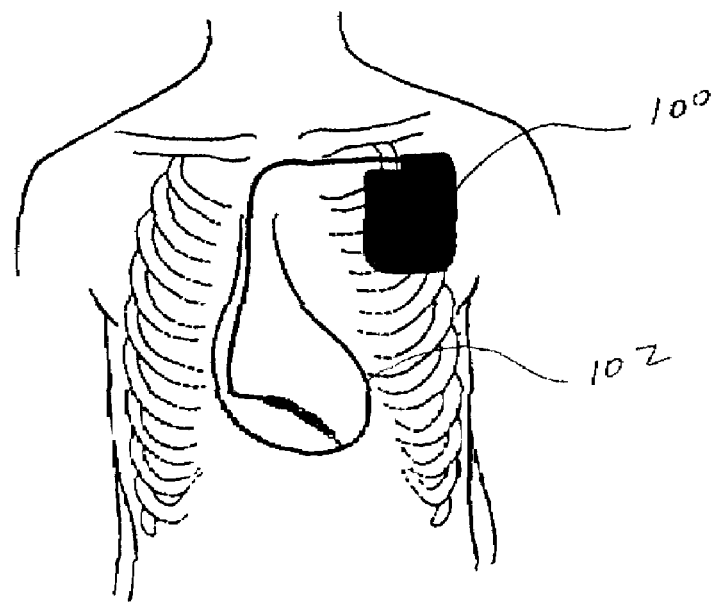
FIGS. 1a, 1b are front and side illustrations of a human torso within which is depicted an implantable cardioverter defibrillator.
Figure 1B:
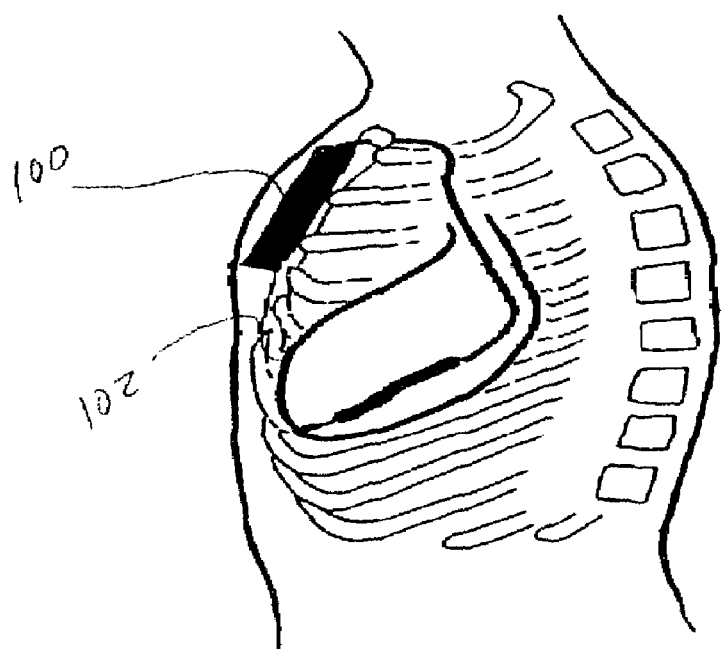
Figure 2:
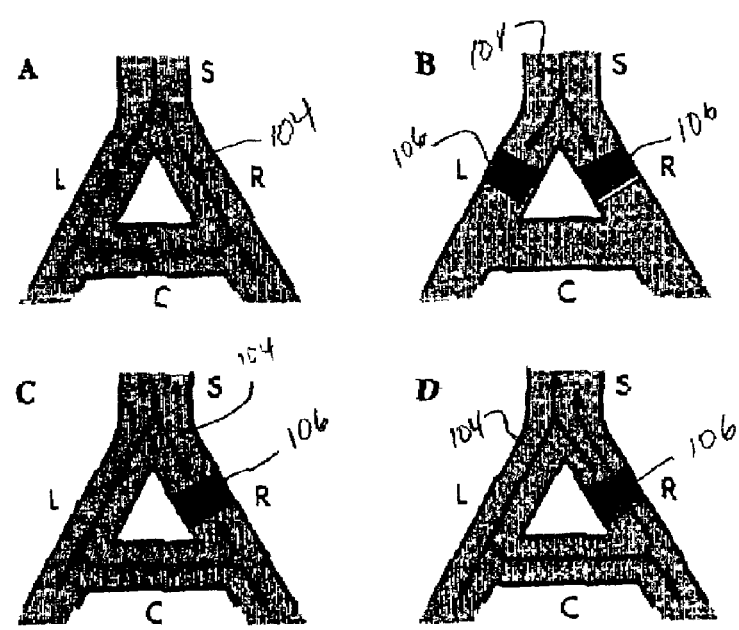
FIGS. 2a-2d are illustrations of the role of a unidirectional block in reentry (the figure is adapted from "Cardiovascular Physiology", by R. M. Berne and M. N. Levy)
Figure 3:
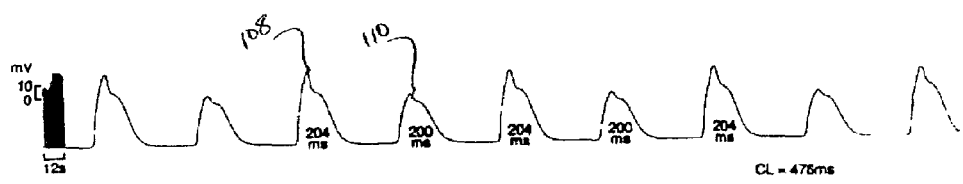
FIG. 3 is an illustration of monophasic action potentials during atrial pacing—alternans after 50 sec of graft occlusion and the progressive development is shown, while interbeat duration shows only a small variation, amplitude changes are striking (adapted from Sutton, PMI, et al. *Eur. Heart J.* 1991;12:70)
Figure 4:
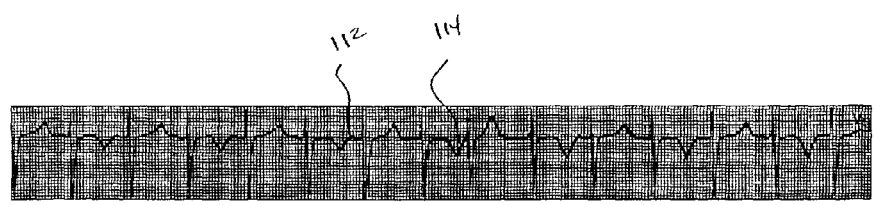
FIG. 4 is a reproduction of a clinical tracing illustrating isolated alternation of the T-wave—the QRS complex is normal in duration, with alternation of polarity of the T-wave (adapted from "Heart Disease", A textbook of cardiovascular medicine, by Eugene Braunwald)

Preferred embodiments of the invention will now be described with reference to the accompanying figures.

A preferred embodiment for this invention involves an apparatus for and method of preventing heart rhythm disturbances that involves detecting (and optionally recording) cardiac electrical activity from electrodes placed in or on the patient's body proximate the patient's heart. The cardiac electrical activity is monitored and beat-to-beat variability in the cardiac electrical activity is measured. A variety of algorithms have been described in the art for measuring variability, including several co-developed by the applicants and described in the following references, which, like all the articles mention in this application, are incorporated herein by reference: Rosenbaum, D S, et al., "Electrical alternans and vulnerability to ventricular arrhythmias", *N Engl J Med.* 1994;3 30:235-41; Adam, D R, et al., "Fluctuations in T-wave morphology and susceptibility to ventricular fibrillation", *J Electrocardiol.* 1984;17:209-18; Smith J M, et al., "Electrical alternans and cardiac electrical instability", *Circulation,* 1988;77:110-21; Chon, et al. "Detection of "noisy" chaos in a time series", *Methods Inf Med.* 1997;36:294-7; and Armoundas, et al. "A stochastic nonlinear autoregressive algorithm reflects nonlinear dynamics of heart-rate fluctuations" *Ann. Biomed. Eng.* 2002;30: 192-201. The measured beat-to-beat variability in the heart's electrical activity provides information on the likelihood of heart rhythm disturbances occurring. The invention uses this information to control therapy to prevent the heart rhythm disturbance from occurring.

In certain preferred embodiments, the beat-to-beat variability is repolarization alternans. As discussed above, repolarization alternans has been well established as a predictor of the development of ventricular arrhythmias. In a method in accordance with the present invention, the level of repolarization alternans can be quantified by means well known in the art, such as measurement of the alternans voltage and measurement of the alternans ratio in one or more electrocardiographic leads. (For a detailed discussion of several known means, refer to either Smith J M, Cohen R J, "Simple finite-element model accounts for wide range of cardiac dysrhythmias", *Proc Natl Acad Sci USA.* 1984;81:233-7, or Electrophysiology TfotEsocatNASoPa, "Heart rate variability, standards of measurement, physiological interpretation and clinical use", *Circulation.* 1996;93:1043-1065. Threshold values of these parameters can be established such as 1.9 microvolts for the alternans voltage and a value of 3.0 for the alternans ratio. When the level of repolarization alternans exceeds a threshold value over some period of time (such as one minute) therapy is delivered to suppress the repolarization alternans and thus reduce the likelihood that a heart rhythm disturbance will occur. Repolarization alternans can be reliably estimated by analysis of approximately 128 beats. Thus, in about a minute or so (assuming a rate of 105-110 beats/min) the number of beats needed in the estimation will have been detected and/or recorded. As previously defined, repolarization alternans as used herein includes any change in the morphology of the T-wave or ST segment of the electrocardiogram on occurring on an every other beat basis. In other embodiments, the beat-to-beat variability in the cardiac electrical activity that is measured is heart rate variability. As discussed above and in Armoundas et al. "A stochastic nonlinear autoregressive algorithm reflects nonlinear dynamics of heart-rate fluctuations", *Ann. Biomed. Eng.* 2002, 30:192-201, reduced heart rate variability is a well known predictor of the development of ventricular arrhythmias. (See also Chon, *Methods Inf Med.* 1997;36:294-7.) For example, a threshold value of heart variability may be established, such as the Standard Deviation of Normal to Normal RR intervals measure of heart rate variability being equal to 60 milliseconds. When the heart rate variability is less than the threshold value for some period of time (e.g., one minute) then therapy is delivered to increase the heart rate variability and thus reduce the likelihood that a heart rhythm disturbance will occur.

The invention provides control over the delivery of one or more therapeutic chemical substances. The chemical substance may be a pharmacological agent that reduces the likelihood of a heart rhythm disturbance from occurring, such as a class III antiarhythmic drug, beta-blocker, or ace inhibitor. The delivery time and dosages are determined on a case-by-case basis based upon a number of patient factors. The substance may be delivered into the blood stream or directly into the heart.

In alternative embodiments, the controlled therapy comprises the delivery of electrical impulses to the heart through electrodes in or on the heart. The electrical impulses may cause the excitation of the cardiac tissue and thus pace the heart. The energy of these impulses is far less than the energy associated with delivery of a defibrillation shock to terminate ventricular fibrillation. Thus these impulses do not cause damage to the heart tissue. In one preferred embodiment the electrical impulses may be delivered at varying inter-impulse intervals so as to increase the level of heart rate variability. For example, the inter-impulse intervals may have a mean of 600 milliseconds and a standard deviation of 120 milliseconds. In general, the mean inter-impulse interval needs to be chosen small enough so that most of the heart beats result from the applied impulses and not from spontaneous cardiac electrical activity. The variable inter-beat intervals will also cause the diastolic intervals associated with cardiac electrical activity in the heart's ventricles to vary. Since the ST and T-wave morphology also depends on the duration of the preceding diastolic interval, the variability in the timing of the electrical impulses will also cause increased variability in ST and T-wave morphology and thus tend to suppress repolarization alternans.

The delivered therapeutic electrical stimulus preferably has a minimum energy level similar to that delivered by pacemakers (pacing pulse), and a maximum energy level similar to that delivered by defibrillators (defibrillation shock) commonly known to those skilled in the field. The therapeutic electrical stimulus should be preferably delivered outside the vulnerable window wherein ventricular fibrillation may be induced.

In another preferred embodiment, when there is alternation in the Beat Duration (duration of time from the beginning of depolarization to the end of repolarization), the electrical impulse is delivered at a time interval after the end of repolarization in the beats with the shorter Beat Duration. This time interval is longer than the diastolic interval that follows the beats with the longer Beat Duration but shorter than the diastolic interval that follows the beats with the shorter Beat Duration. Among the heart rhythm disturbances that are being prevented are tachyarrhythmias and bradyarrhythmias. Tachyarrhythmias that are of particularly severe risk to a patient are ventricular tachycardia or ventricular fibrillation. Both of these tachyarrhythmias may be fatal if untreated.

In preferred embodiments the electrical activity of the heart is detected and recorded from a passive electrode within the heart. Such electrodes may be placed in the atrium, ventricle or coronary sinus of the heart.

The beat-to-beat variability measurement may be performed in an implanted device such as an implantable cardioverter defibrillator or cardiac pacemaker. Such devices contain miniature microprocessors capable of performing the computations necessary for the measurement. As discussed above, a variety of algorithms for computing the variability based upon repolarization alternans or heart rate variability are known to those skilled in the field, and several are described in the references cited and incorporated in this application. These devices can both implement the method of this invention and serve also as a cardioverter defibrillator or pacemaker.

Figure 5:
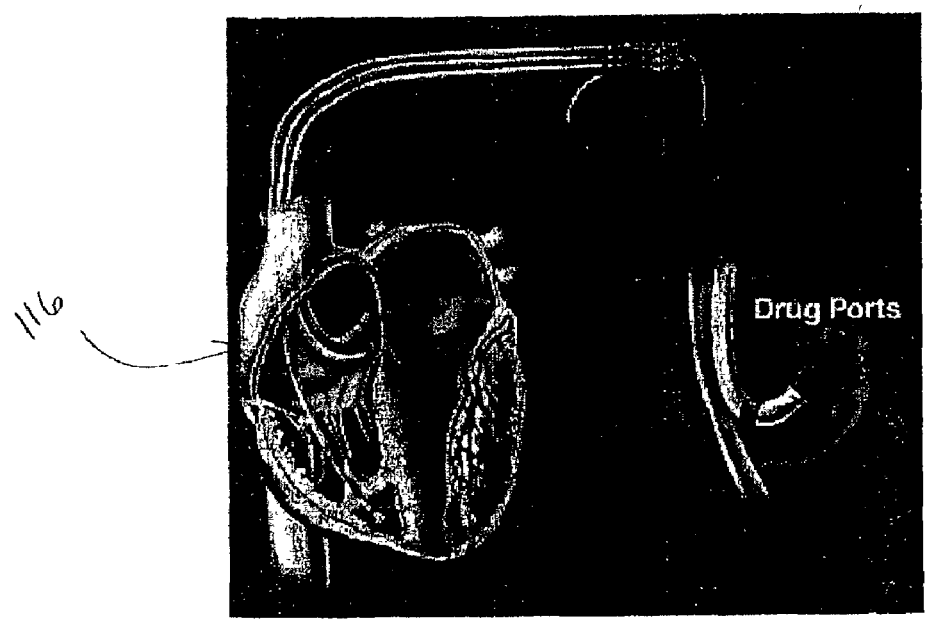
FIG. 5 is an illustration of an ICD having drug ports for therapy delivery in accordance with certain embodiments of the present invention.

The therapy in certain embodiments is also delivered by the implanted device. For example the implantable device can incorporate the means for generating electrical stimulating pulses of specified energies and applying the pulses to body tissue at specified times, and deliver the impulses used for pacing the heart at the appropriate times and energy levels that are selected as described above. In another preferred embodiment such devices can contain a reservoir of chemical compound and delivery means, and deliver the compound to the patient at the appropriate times and dosages whose selection is likewise described above. An ICD 116 equipped with drug ports is illustrated in FIG. 5 as an exemplary embodiment of the present invention.

In a preferred embodiment the measured beat-to-beat variability in cardiac electrical activity (i.e. instantaneous measuremento of of repolarization alternans and/or heart rate variability) to identify periods when there is an increased probability that a heart rhythm disturbance may occur will be compared to a baseline level of repolarization alternans measured prior to the patient's discharge from the hospital.

Other embodiments of the invention will be apparent to those skilled in the art from a consideration of the specification or practice of the invention disclosed herein. It is intended that the specification and examples herein be considered as exemplary only, with the true scope and spirit of the invention being indicated by the following claims.

We claim:

1. Method of preventing heart rhythm disturbances comprising:
   detecting cardiac electrical activity;
   analyzing the cardiac electrical activity to measure beat-to-beat variability in the morphology of electrocardiographic waveforms; and
   using the measured beat-to-beat variability in the morphology of the electrocardiographic waveforms to control an intervention that modifies the morphology of the electrocardiographic waveforms on a beat-to-beat basis in order to alter the beat-to-beat variability in the morphology in the electrocardiographic waveforms in order to reduce the likelihood of the heart rhythm disturbance.

2. The method of claim 1 wherein beat-to-beat variability in the cardiac electrical activity comprises altenans.

3. The method of claim 1 wherein the beat-to-beat variability in the cardiac electrical activity comprises repolarization altenans.

4. The method of claim 1 wherein the using step comprises the delivery of one or more chemical substances.

5. The method of claim 1 wherein the using step comprises the delivery of electrical impulses to the heart.

6. The method of claim 5 wherein the electrical impulses are controlled to alter the variability in the diastolic interval.

7. The method of claim 5 wherein the electrical impulses are controlled to alter the variability in the repolarization.

8. The method of claims 5 or 6 wherein the electrical impulses reduce repolarization altenans.

9. The method of claim 6 wherein the cardiac electrical activity comprises alternating beats of short and long duration; and the electrical impulses are delivered in a time interval after the end of repolarization of one or more of the beats having short beat durations, the time interval being longer than the diastolic interval that follows the beats with the longer beat duration but shorter than the diastolic interval that follows the beats with the shorter beat duration.

10. The method of claim 1 wherein the heart rhythm disturbance is a tachyarrhythmia.

11. The method of claim 1 wherein the heart rhythm disturbance is a bradyarrhythmia.

12. The method of claim 1 further comprising recording the cardiac electrical activity through at least one passive electrode within the heart.

13. The method of claim 1 wherein the measuring step is performed by an implanted device.

14. The method of claim 1 wherein the using step is delivered by an implanted device.

15. The method of claims 13 or 14 wherein the implanted device serves as a cardiac pacemaker or a cardiac cardioverter/defibrillator.

16. The method of claim 14 wherein the implantable device has means for generating electrical stimulating pulses of specified energies and applying the pulses to body tissue at specified times.

17. The method of claims 13 or 14 wherein settings of the implanted device may be adjusted remotely through a telemetry communication system.

18. The method of claim 1 wherein the measuring step further involves identifying periods where there is an increased probability that a heart rhythm disturbance may occur.

19. The method of claim 18 wherein the using step involves delivering of therapy during the identified periods.

20. The method of claim 1 further comprising the step of adjusting threshold values used in the measuring or modifying steps for individual subjects.

21. Apparatus for the prevention of a heart rhythm disturbance comprising:
a cardiac electrical activity detector;
circuitry that receives and analyzes the cardiac electrical activity to measure beat-to-beat variability in the morphology of electrocardiographic waveforms; and
control means using the measured beat-to-beat variability in the morphology of the electrocardiographic waveforms to control an intervention that modifies the morphology of electrocardiographic waveforms on a beat-to-beat basis in order to alter the beat-to-beat variability in the morphology of the electrocardiographic waveforms in order to reduce the likelihood of heart rhythm disturbance occurrence.

22. The apparatus of claim 21 wherein the beat-to-beat variability in the cardiac electrical activity comprises altenans.

23. The apparatus of claim 21 wherein the beat-to-beat variability comprises repolarization altenans.

24. The apparatus of claim 21 wherein the control means comprises the delivery of one or more chemical substances.

25. The apparatus of claim 21 wherein the control means comprises the delivery of electrical impulses to the heart.

26. The apparatus of claim 25 wherein the delivered electrical impulses alter the variability in the diastolic interval.

27. The apparatus of claim 26 wherein the delivered electrical impulses reduce repolarization altenans.

28. The apparatus of claim 26 wherein the electrical impulses are delivered in the diastolic interval following a short beat and prior to the end of repolarization of a subsequent long beat.

29. The apparatus of claim 21 wherein the heart rhythm disturbance is a tachyarrhythmia.

30. The apparatus of claim 21 wherein the heart rhythm disturbance is a bradyarrhythmia.

31. The apparatus of claim 21 wherein the cardiac electrical activity detector further comprises at least one passive electrode within the heart and electrical activity recording means.

32. The apparatus of claim 21 wherein the measuring circuitry is incorporated into an implanted device.

33. The apparatus of claim 21 wherein the control means modifies the beat-to-beat variability by an implanted device.

34. The apparatus of claim 32 or 33 wherein the implanted device serves as a cardiac pacemaker or a cardiac cardioverter/defibrillator.

35. The apparatus of claim 33 wherein the implantable device has means for generating electrical stimulating pulses of specified energies and applying the pulses to body tissue at specified times.

36. The apparatus of claims 32 or 33 further comprising a telemetry communications system for remotely adjusting settings of the implanted device.

37. The apparatus of claim 21 wherein the circuitry provides identification of periods when there is an increased probability that a heart rhythm disturbance may occur.

38. The apparatus of claim 37 wherein the control means delivers therapy during the identified periods.

39. The apparatus of claim 21 further comprising an adjuster for adjusting for individual subjects' threshold values employed by the circuitry and control means.

* * * * *